United States Patent
Holmberg

(10) Patent No.: US 10,239,810 B2
(45) Date of Patent: Mar. 26, 2019

(54) PROCESS FOR ALDEHYDE MANUFACTURE

(71) Applicant: JOHNSON MATTHEY PUBLIC LIMITED COMPANY, London (GB)

(72) Inventor: Johan Björn Mattias Holmberg, Perstorp (SE)

(73) Assignee: Johnson Matthey Public Limited Company, London, England (GB)

( * ) Notice: Subject to any disclaimer, the term of this patent is extended or adjusted under 35 U.S.C. 154(b) by 0 days.

(21) Appl. No.: 15/570,854

(22) PCT Filed: Apr. 28, 2016

(86) PCT No.: PCT/GB2016/051217
§ 371 (c)(1),
(2) Date: Oct. 31, 2017

(87) PCT Pub. No.: WO2016/177999
PCT Pub. Date: Nov. 10, 2016

(65) Prior Publication Data
US 2018/0148399 A1 May 31, 2018

(30) Foreign Application Priority Data
May 1, 2015 (GB) .................................. 1507595.5

(51) Int. Cl.
*C07C 45/38* (2006.01)
(52) U.S. Cl.
CPC .................................. *C07C 45/38* (2013.01)
(58) Field of Classification Search
CPC .................................................. C07C 45/38
USPC ....................................................... 568/474
See application file for complete search history.

(56) References Cited

U.S. PATENT DOCUMENTS

| 3,236,782 | A | 2/1966 | Koch |
| 3,277,179 | A | 10/1966 | Sze |
| 3,965,194 | A | 6/1976 | Sze et al. |
| 4,343,954 | A | 8/1982 | Hoene |
| 4,471,141 | A | 9/1984 | Windawl et al. |
| 2012/0071688 | A1 | 3/2012 | Herzog et al. |

FOREIGN PATENT DOCUMENTS

| DE | 2630928 A1 | 1/1978 |
| EP | 2213370 A2 | 8/2010 |
| GB | 2518274 A | 3/2015 |

OTHER PUBLICATIONS

GB1507583.1, Search Report Under 17(5) dated Feb. 8, 2016.
Soares, A.P.V. et al., "Mechanism of Deactivation of Iron-Molybdate Catalysts Prepared by Coprecipitation and Sol-Gel Techniques in Methanol to Formaldehyde Oxidation," Chemical Engineering Science, vol. 58, No. 7, Apr. 1, 2003, pp. 1315-1322.
Li Jin-Lu, et al., "Improvement in Reactivity, Reproducibility and Stability of Fe-Mo Catalysts by Wet Mixing," Catalysis Today, vol. 51, Jan. 1, 1999, pp. 195-199.
PCT/GB2016/051217, International Search Report dated Jul. 4, 2016.
PCT/GB2016/051217, Written Opinion dated Jul. 4, 2016.
K.Ivanov et al., Optimization of the Methanol Oxidation Over Iron-Molybdate Catalysts, Chemical Engineering Journal, 154 (2009), pp. 189-195.

*Primary Examiner* — Sikarl A Witherspoon
(74) *Attorney, Agent, or Firm* — BakerHostetler

(57) ABSTRACT

The process of the invention is a process for the production of an aldehyde from the corresponding alcohol comprising the steps of feeding to a reactor a feed stream comprising said alcohol and an oxygen-containing gas; reacting said alcohol in the gas phase with said oxygen-containing gas in said reactor in the presence of a catalyst comprising oxides of iron and molybdenum, wherein the process further comprises the step of adding water to said feed stream. The process is particularly useful for the production of formaldehyde by the oxidation of methanol.

11 Claims, No Drawings

PROCESS FOR ALDEHYDE MANUFACTURE

CROSS-REFERENCE TO RELATED APPLICATIONS

This application is a National Stage of International Patent Application No. PCT/GB2016/051217 filed Apr. 28, 2016, which claims the benefit of Great Britain Patent Application No. 1507595.5 filed May 1, 2015, the disclosures of each of which are incorporated herein by reference in their entireties for any and all purposes.

The invention concerns a process, in particular for the oxidation of an alcohol to produce an aldehyde, for example the oxidation of methanol for the manufacture of formaldehyde.

Processes for the manufacture of formaldehyde in which methanol is oxidised over a catalyst have been well-known for many years. One well-known process includes the oxidation of methanol over a mixed oxide catalyst, usually containing oxides of iron and molybdenum: $CH_3OH + 0.5O_2 \rightarrow CH_2O + H_2O$. Plants operating this process usually operate at a reactor inlet pressure of about 1 bar G or less. Although it would be desirable to increase the production from a plant by increasing the pressure at which the process is operated, this can result in problems due to a loss in selectivity of the catalyst. The result is an increase in formation of unwanted by-products such as dimethyl ether (DME) believed to be formed from an increase in the concentration of methoxy groups adsorbed onto the catalyst surface:

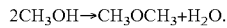

$2CH_3OH \rightarrow CH_3OCH_3 + H_2O$.

Although the DME formation may be reduced by increasing the reaction temperature, higher temperatures may have a detrimental effect on the catalyst lifetime. It is therefore desirable to produce a process and catalyst which can be operated at relatively high pressures whilst alleviating the loss of selectivity which such operation may otherwise entail. The process of the invention is intended to provide one solution to this problem.

According to the invention a process for the production of an aldehyde from the corresponding alcohol comprises the steps of feeding to a reactor a feed stream comprising said alcohol and an oxygen-containing gas; reacting said alcohol in the gas phase with said oxygen-containing gas in said reactor in the presence of a catalyst comprising oxides of iron and molybdenum, characterised in that the process further comprises the step of adding water to said feed stream.

The reactor may be operated at an inlet pressure suitable to the particular process and the plant equipment available. The skilled person must select an appropriate reactor pressure based on the plant and the desired outcome. A typical process plant for formaldehyde production using a mixed iron-molybdenum oxide catalyst may be operated at a reactor inlet pressure of about 1 bar G. Bar G indicates gauge pressure in bar, i.e. the pressure above atmospheric pressure. Bar G may be converted to bar absolute by adding the local atmospheric pressure in bar. Using the process of the invention the reactor inlet pressure may be at least 0.4 bar G. It is a particular benefit of the process of the invention that the reactor inlet pressure may be increased without increasing the rate of formation of ether significantly. Therefore the reactor inlet pressure may be at least 1.0 bar G, especially greater than 1.5 bar G, particularly greater than 3 bar G and may be up to 10 bar G or higher than 10 bar G, if suitable process equipment is available.

The oxygen-containing gas may be any suitable gas stream. The concentration of oxygen in the reactor is usually selected by the process designer according to the process which is intended. For example, the oxygen concentration may be selected so that the mixture of oxygen and organic compounds is not explosive. In a typical formaldehyde-producing process, the oxygen-containing gas is air. The oxygen-containing gas may be mixed with the alcohol and other components of the feed stream, such as a recycled stream, either within the reactor, at the reactor inlet or before the feed stream is fed through the reactor inlet.

The feed stream may comprise alcohol at a concentration of from 1% to 20% by volume of said feed stream. The feed stream may comprise from 3% to 15% by volume of alcohol, for example from about 6 vol % to about 12 vol %. The alcohol may comprise methanol or ethanol. Other alcohols may also be reacted using the process of the invention.

In a typical process the reaction products which leave the reactor which contain some of the product aldehyde are treated to separate a portion of the product aldehyde from other compounds present in the product stream. Such other products usually include unreacted alcohol, water, carbon monoxide, dialkyl ether and nitrogen, if added for example if the oxygen-containing gas used is air. A portion of the treated product stream may be recycled to the reactor. In such a case, the feed stream to the reactor may contain dialkyl ether made as a by-product in the reactor. It is known that when dialkyl ether is added to the reactor, the amount of dialkyl ether made in the reaction tends to be less. The feed stream may contain up to about 0.7 vol % of dialkyl ether. Typically the feed stream may contain from about 0.2 to about 0.6 vol % of dialkyl ether. Dialkyl ether present in the feed stream is usually present as a result of feeding a recycled product stream to the reactor. When the process is a process for making formaldehyde from the reaction of methanol with oxygen, the dialkyl ether is dimethyl ether (DME). Conversion of methanol to dimethyl ether is a known problem which affects the productivity of formaldehyde processes, particularly when operated at higher inlet pressures.

We have found that the presence of water in the feed stream to the reactor reduces the amount of dialkyl ether which is formed. The water may be added to the feed stream by adding water to a vaporiser in which the alcohol is vaporised prior to feeding into the reactor. The water may be added to the methanol feed, for example prior to a vapourisation step. The water may be added to the feed stream as steam. Water may also be present in a recycled product stream. The amount of water present in the recycled stream depends on the process steps carried out downstream of the reactor from which the recycled stream is taken. In a formaldehyde plant the downstream processes typically include a step of absorbing the formaldehyde-containing product stream in a liquid, which may be water or a urea solution to form a formaldehyde-containing solution. The absorption process is typically carried out in a gas-liquid absorption tower, or absorber. The conditions in the absorber, particularly at the gas exit (typically the top) of the absorber determine the amount of water contained in the gas which may be recycled to the alcohol-oxidation reactor. As an example, in a typical process, operating in ambient conditions of 20° C. and 70% relative humidity, when the absorber top temperature is 40° C., and the absorber top pressure is 0.3 bar G, then the amount of water in the gas leaving the absorber may be about 3.8% by volume. If the absorber top temperature is decreased, or the absorber top pressure is increased, then the amount of water in the gas leaving the absorber decreases. Therefore when the process of the invention is operated at relatively high pressures, which is desirable in order to increase the rate of output of aldehyde from the reactor, the addition of water to the feed stream has the benefit of reducing the amount of dialkyl ether which is formed. Preferably sufficient water is added to the feed stream to bring the amount of water in the feed stream to a value in the range of from 3.0 to 15.0 vol % of water, preferably 3.5 to 10.0 vol %. The step of adding water to the feed stream does not include any step of adding a recycled product stream containing water. Although a recycled product stream may be used and such a recycle stream usually contains water, the invention is directed towards adding additional water because at higher operating pressure the amount of water in a recycle stream is insufficient to carry out the process of the invention.

The catalyst comprises oxides of iron and molybdenum. A typical catalyst used in the oxide process is a mixture of iron molybdate ($Fe_2(MoO_4)_3$) and molybdenum trioxide ($MoO_3$) with a Mo:Fe atomic ratio between 2 and 3. The catalyst may optionally contain oxides of other metals such as vanadium, aluminium, silicon, calcium, cobalt, chromium, copper, magnesium, manganese, nickel, zinc and titanium. Suitable catalysts may have a specific surface area of about 2-20 $m^2$/g, for example 3-10 $m^2$/g. The catalyst may take any conventional physical form. Rings, saddles and spheres are examples of catalyst particle shapes which are known and used in the field. A typical commercial catalyst comprises rings of outer diameter approximately 4-6 mm and a length approximately 2-5 mm In a particular embodiment of the invention the catalyst comprises an alkali metal or an alkaline earth metal, such as sodium, potassium, magnesium and calcium. Alkali metal (or alkaline earth metal) may be added to the catalyst by any suitable method. When the catalyst is made by precipitation from a solution of soluble iron and molybdenum salts, the precipitate usually contains alkali metal when the precipitating agent is a solution of an alkali metal compound, such as sodium hydroxide or sodium carbonate, for example. In conventional preparations, this alkali metal is removed by washing with water to a specified concentration of alkali metal. In the preparation of a catalyst for use in the process of the invention, the alkali metal may be allowed to remain in such a precipitated catalyst at a higher concentration than usual, by controlling the amount that is removed by washing. Optionally an alkali(ne earth) metal compound could be added to the wash water to increase the amount of alkali(ne earth) metal in the catalyst. Upon subsequent calcination of the catalyst, the alkali(ne earth) metal may be converted to an oxide and may form a mixed oxide with the iron and/or the molybdenum or other metal which may be present. When the alkali(ne earth) metal is added to the catalyst during a precipitation step, the amount of alkali metal in the finished catalyst may be from 50 to 1000 ppm by weight of said alkali metal, for example from 50-250 ppm by weight, based on the total catalyst weight Alkali metal may be added to a catalyst by impregnation with a solution of a soluble alkali metal salt, such as sodium hydroxide and then dried. The impregnated catalyst may optionally be calcined. When prepared by impregnating a formed metal oxide catalyst with a solution of an alkali(ne earth) metal salt the catalyst may comprise from 50 to 300 ppm by weight of said alkali(ne earth) metal, for example from 50-250 ppm by weight, based on the total catalyst weight, A preferred process according to the invention comprises the oxidation of methanol to produce formaldehyde. Another preferred process comprises the oxidation of ethanol to produce acetaldehyde.

The reaction temperature is typically greater than 250° C., normally between 250° C. and 400° C. The reactor feed inlet temperature may typically range from about 60° C. to about 220° C. The reaction temperature may vary along the length of the reactor bed. Normally the reactor is operated such that the temperature is higher at a location between the inlet and the outlet parts of the reactor. The reaction temperature in different parts of the reactor may be affected by the composition of catalyst in the catalyst bed. A mixed catalyst bed may be used, in which a catalyst may be mixed with an inert material or with a catalyst of a different composition and activity to provide a desired activity profile across the catalyst bed. The reaction temperature may be controlled by means of a heat transfer system. The reactor temperature may be varied over time. A typical catalyst tends to lose activity over its useful lifetime. The reactor temperature may be varied to take account of such a loss in activity.

In a typical embodiment, the reactor comprises a reaction tube supplied with a heat transfer system. More than one reactor may be employed in parallel or in series. A commercial process plant may comprise a plurality of reaction tubes, each containing a bed of catalyst particles and each being in thermal contact with a heat transfer system. The process plant may comprise more than 100, and frequently several thousand such reaction tubes.

The invention will be further described in the following examples.

EXAMPLE 1

A single tube reactor (21.2 mm inner diameter, length 1655 mm) was charged with a mixed bed of a commercial catalyst comprising iron molybdate ($Fe_2(MoO_4)_3$) and molybdenum trioxide ($MoO_3$) with a Mo:Fe atomic ratio of 2.5 mixed with an inert material to provide a standard reaction profile through the bed. The reactor was equipped with 10 radial thermocouples inserted into the catalyst bed spaced at approximately equal distances along the bed.

The feed consisted of dry air and nitrogen fed by mass flow controller and water and methanol feed by two separate pumps. The product stream, sampled at the reactor exit, is analysed by gas chromatography. The gases were preheated to approx. 200 C°. The liquid was preheated to 55 C.° before being mixed in the vaporizer, in which the feed is vaporized and heated to around 200 C.° which is the reactor inlet temperature. The tube is cooled by a heat transfer oil system operating according to the thermosiphon principle.

The reaction was operated at a total gas inlet flow of 66.90 Nl/min with various inlet concentrations of water and DME, and fixed oxygen and methanol concentrations of 11.0 vol % (in dry gas) and 10.0 vol %, respectively, with nitrogen as balance. The DME level in the feed was varied from 0% to 0.27% because when a commercial plant is operated with a recycle stream, the feed contains some DME.

All tests were performed with a reactor inlet pressure of 1.69 bar g. The water content and DME content of the feed stream were varied, keeping the oxygen and methanol content and pressure fixed. The pressure in the heat transfer system was varied so as to vary the temperature of the oil and compensate for the impact of the water which has a negative impact on the activity. The operating conditions for the tests for the different catalyst conditions are presented in Table 1. In the Table: DME=dimethyl ether, MeOH=methanol, FA=formaldehyde, HTF=temperature of the heat transfer fluid, max=maximum temperature measured in the reactor tube.

The results show that as the amount of water in the feed is increased from 2.6% to 7.6%, at any given initial concentration of DME, the DME yield falls. DME is an unwanted by-product and represents a loss of potential formaldehyde yield. This effect is noticed over the range of operating temperatures used.

TABLE 1

| Concentration in feed (vol %) | | Yield and Losses (single pass) (%) | | | | Temperature (° C.) | |
|---|---|---|---|---|---|---|---|
| DME | $H_2O$ | MeOH | CO | DME | FA | HTF | max |
| 0 | 2.6 | 3.0 | 4.6 | 3.6 | 88.8 | 266 | 350 |
| 0 | 2.6 | 3.0 | 4.7 | 3.4 | 88.8 | 268 | 346 |
| 0 | 5.1 | 2.4 | 5.0 | 3.4 | 89.2 | 268 | 374 |
| 0 | 5.1 | 2.8 | 4.6 | 3.4 | 89.2 | 270 | 358 |
| 0 | 5.1 | 3.0 | 4.6 | 3.4 | 89.0 | 272 | 358 |
| 0 | 7.6 | 2.6 | 5.1 | 3.2 | 89.2 | 274 | 366 |
| 0 | 7.6 | 2.9 | 5.0 | 3.2 | 88.9 | 276 | 362 |
| 0.15 | 2.6 | 3.1 | 4.6 | 3.1 | 89.1 | 266 | 351 |
| 0.15 | 2.6 | 3.2 | 4.6 | 3.0 | 89.1 | 268 | 346 |
| 0.15 | 5.1 | 2.6 | 5.0 | 2.7 | 89.7 | 268 | 378 |
| 0.15 | 5.1 | 2.9 | 4.6 | 2.7 | 89.7 | 270 | 377 |
| 0.15 | 5.1 | 3.1 | 4.5 | 2.8 | 89.5 | 272 | 358 |
| 0.15 | 7.6 | 2.8 | 5.0 | 2.5 | 89.7 | 274 | 368 |
| 0.15 | 7.6 | 2.9 | 5.1 | 2.6 | 89.4 | 276 | 361 |
| 0.27 | 2.6 | 3.2 | 4.6 | 2.8 | 89.4 | 266 | 351 |
| 0.27 | 2.6 | 3.3 | 4.6 | 2.8 | 89.3 | 268 | 349 |
| 0.27 | 5.1 | 2.4 | 5.4 | 2.2 | 90.0 | 268 | 379 |
| 0.27 | 5.1 | 2.6 | 5.2 | 2.4 | 89.8 | 270 | 363 |
| 0.27 | 5.1 | 2.9 | 5.1 | 2.4 | 89.6 | 272 | 358 |
| 0.27 | 7.6 | 2.7 | 5.2 | 2.2 | 89.9 | 274 | 369 |
| 0.27 | 7.6 | 2.8 | 5.1 | 2.2 | 89.9 | 276 | 360 |

EXAMPLE 2

A fresh sample of the commercial catalyst used in Example 1 was modified by impregnation with sodium hydroxide. 0.15 g NaOH (50%) and 41.2 g methanol was added to 200 g catalyst. The solvent was evaporated at room temperature overnight. The catalyst contained 275 ppm Na.

The catalyst was used to prepare a mixed catalyst bed in the reactor used in Example 1. The modified catalyst was used in the first quarter of the catalyst bed. The remainder of the catalyst bed was made using unmodified catalyst, as used in Example 1. The reaction was operated using the conditions set out in Example 1 and the results are shown in Table 2.

The beneficial effect of water on the DME loss is also seen in Table 2. In addition, the sodium-modified catalyst appears to have reduced the amount of DME loss even further.

TABLE 2

| Concentration in feed (vol %) | | Yield and Losses (single pass) (%) | | | | Temperature (° C.) | |
|---|---|---|---|---|---|---|---|
| DME | $H_2O$ | MeOH | CO | DME | FA | HTF | max |
| 0 | 2.6 | 3.0 | 4.8 | 3.0 | 89.3 | 268 | 359 |
| 0 | 5.1 | 2.5 | 5.1 | 3.0 | 89.4 | 268 | 368 |
| 0 | 5.1 | 2.5 | 4.9 | 3.0 | 89.6 | 270 | 361 |
| 0 | 5.1 | 2.7 | 4.9 | 2.7 | 89.6 | 272 | 362 |
| 0 | 7.6 | 2.6 | 5.0 | 2.8 | 89.6 | 272 | 370 |
| 0 | 7.6 | 2.8 | 4.6 | 2.7 | 89.8 | 274 | 361 |
| 0 | 7.6 | 2.8 | 4.8 | 2.6 | 89.8 | 276 | 369 |
| 0.15 | 2.6 | 3.0 | 4.9 | 2.3 | 89.9 | 268 | 358 |
| 0.15 | 5.1 | 2.7 | 5.0 | 2.5 | 89.8 | 268 | 368 |
| 0.15 | 5.1 | 2.8 | 4.8 | 2.7 | 89.7 | 270 | 360 |
| 0.15 | 5.1 | 2.9 | 4.8 | 2.5 | 89.8 | 272 | 361 |
| 0.15 | 7.6 | 2.7 | 5.0 | 2.4 | 90.0 | 272 | 368 |
| 0.15 | 7.6 | 2.9 | 4.7 | 2.5 | 89.9 | 274 | 361 |
| 0.15 | 7.6 | 2.9 | 4.6 | 1.8 | 90.6 | 276 | 367 |
| 0.27 | 2.6 | 3.1 | 4.7 | 2.0 | 90.3 | 268 | 358 |
| 0.27 | 5.1 | 2.5 | 5.1 | 2.2 | 90.2 | 268 | 369 |
| 0.27 | 5.1 | 2.8 | 4.8 | 1.8 | 90.6 | 270 | 362 |
| 0.27 | 5.1 | 2.8 | 4.9 | 2.0 | 90.3 | 272 | 360 |
| 0.27 | 7.6 | 2.6 | 5.0 | 1.9 | 90.5 | 272 | 369 |
| 0.27 | 7.6 | 2.8 | 4.8 | 1.6 | 90.8 | 274 | 364 |
| 0.27 | 7.6 | 2.9 | 4.8 | 2.0 | 90.4 | 276 | 363 |

EXAMPLE 3

The experiment of Example 1 was repeated using a catalyst made according to the method in Example 2, which had been used over a period of time and having a specific production of about 15 MT of 37% formaldehyde per kg of catalyst.

The data, presented in Table 3, shows that for any given concentration of DME in the feed stream, the amount of DME made in the process falls as the concentration of water in the feed stream is raised. This leads to an increase in the yield of formaldehyde.

TABLE 3

| Concentration in feed (vol %) | | Yield and Losses (single pass) (%) | | | | Temperature (° C.) | |
|---|---|---|---|---|---|---|---|
| DME | $H_2O$ | MeOH | CO | DME | FA | HTF | max |
| 0 | 2.6 | 1.8 | 4.8 | 4.4 | 89.0 | 286 | 396 |
| 0 | 2.6 | 1.5 | 4.9 | 4.5 | 89.1 | 289 | 400 |
| 0 | 2.6 | 1.3 | 5.0 | 4.5 | 89.2 | 292 | 403 |
| 0 | 5.1 | 2.5 | 4.7 | 3.6 | 89.2 | 286 | 402 |
| 0 | 5.1 | 1.8 | 5.1 | 3.7 | 89.4 | 289 | 402 |
| 0 | 5.1 | 1.6 | 5.2 | 3.8 | 89.5 | 292 | 406 |
| 0 | 7.6 | 2.2 | 5.1 | 3.4 | 89.4 | 289 | 414 |
| 0 | 7.6 | 1.9 | 5.1 | 3.4 | 89.7 | 292 | 409 |
| 0 | 7.6 | 1.7 | 5.0 | 3.2 | 90.1 | 295 | 408 |
| 0.15 | 2.6 | 2.0 | 4.5 | 3.8 | 89.6 | 286 | 400 |
| 0.15 | 2.6 | 1.8 | 4.7 | 3.8 | 89.7 | 289 | 398 |
| 0.15 | 2.6 | 1.5 | 4.8 | 3.8 | 89.9 | 292 | 403 |
| 0.15 | 5.1 | 2.4 | 5.0 | 3.3 | 89.3 | 286 | 405 |
| 0.15 | 5.1 | 1.9 | 5.1 | 3.1 | 89.9 | 289 | 400 |
| 0.15 | 5.1 | 1.7 | 5.2 | 3.1 | 90.0 | 292 | 408 |
| 0.15 | 7.6 | 2.6 | 4.9 | 2.3 | 90.2 | 289 | 405 |
| 0.15 | 7.6 | 1.9 | 5.0 | 2.3 | 90.9 | 292 | 408 |
| 0.15 | 7.6 | 1.7 | 5.1 | 2.3 | 91.0 | 295 | 407 |
| 0.27 | 2.6 | 2.0 | 4.5 | 3.2 | 90.2 | 286 | 398 |
| 0.27 | 2.6 | 1.7 | 4.8 | 3.3 | 90.2 | 289 | 398 |
| 0.27 | 2.6 | 1.6 | 4.8 | 3.2 | 90.4 | 292 | 402 |
| 0.27 | 5.1 | 2.4 | 5.1 | 2.8 | 89.7 | 286 | 405 |
| 0.27 | 5.1 | 2.0 | 5.1 | 2.7 | 90.2 | 289 | 403 |
| 0.27 | 5.1 | 1.7 | 5.2 | 2.8 | 90.3 | 292 | 406 |
| 0.27 | 7.6 | 2.5 | 5.1 | 1.8 | 90.7 | 289 | 407 |
| 0.27 | 7.6 | 2.0 | 5.1 | 2.0 | 90.9 | 292 | 409 |
| 0.27 | 7.6 | 1.7 | 5.1 | 1.6 | 91.6 | 295 | 408 |

The invention claimed is:

1. A process for the production of an aldehyde from the corresponding alcohol, comprising:
    feeding to a reactor a feed stream comprising said alcohol and an oxygen-containing gas;
    reacting said alcohol in the gas phase with said oxygen-containing gas in said reactor in the presence of a catalyst comprising oxides of iron and molybdenum, wherein said catalyst comprises an alkali metal or an alkaline earth metal in addition to said oxides of iron and molybdenum; and adding water to said feed stream.

2. The process according to claim 1, wherein said reactor is operated at an inlet pressure of at least 1.5 bar G.

3. The process according to claim 1, wherein said oxygen-containing gas is air.

4. A process according to claim 1, wherein a portion of said feed stream comprises a recycled product stream from said process.

5. The process according to claim 1, wherein said feed stream comprises an alkyl ether.

6. The process according to claim 5, wherein said feed stream comprises at most 3% by volume of said alkyl ether.

7. The process according to claim 1, wherein water is added to said feed stream in an amount to produce a feed stream comprising water at a concentration of from 3% to 10% by volume of said feed stream.

8. The process according to claim 1, wherein said feed stream comprises alcohol at a concentration of from 1% to 20% by volume of said feed stream.

9. The process according to claim 1, wherein said catalyst comprises from 50 to 300 ppm by weight of said alkali metal or alkaline earth metal.

10. The process according to claim 1, wherein said alkali metal is sodium.

11. The process according to claim 1, comprising reacting methanol with the oxygen-containing gas such that said alcohol comprises methanol and said aldehyde comprises formaldehyde.

* * * * *